(12) United States Patent
Imagawa et al.

(10) Patent No.: US 10,745,628 B2
(45) Date of Patent: Aug. 18, 2020

(54) HYDROGENATION CATALYST FOR AROMATIC HYDROCARBON AND HYDROTREATMENT METHOD USING THE CATALYST

(71) Applicant: CHIYODA CORPORATION, Yokohama-shi, Kanagawa (JP)

(72) Inventors: Kenichi Imagawa, Yokohama (JP); Haruto Kobayashi, Yokohama (JP); Akihiro Muto, Yokohama (JP); Shinichi Inoue

(73) Assignee: CHIYODA CORPORATION, Yokohama-Shi, Kanagawa (JP)

( * ) Notice: Subject to any disclaimer, the term of this patent is extended or adjusted under 35 U.S.C. 154(b) by 0 days.

(21) Appl. No.: 15/700,089

(22) Filed: Sep. 9, 2017

(65) Prior Publication Data

US 2017/0369793 A1  Dec. 28, 2017

Related U.S. Application Data

(63) Continuation of application No. PCT/JP2016/059106, filed on Mar. 23, 2016.

(30) Foreign Application Priority Data

Mar. 24, 2015  (JP) .................. 2015-060801

(51) Int. Cl.
*C10G 45/48* (2006.01)
*B01J 23/755* (2006.01)
(Continued)

(52) U.S. Cl.
CPC .............. *C10G 45/48* (2013.01); *B01J 21/04* (2013.01); *B01J 21/063* (2013.01); *B01J 23/755* (2013.01);
(Continued)

(58) Field of Classification Search
CPC .... C10G 45/48; C01F 7/34; C01F 7/02; B01J 23/755; B01J 37/18; C07C 5/10;
(Continued)

(56) References Cited

U.S. PATENT DOCUMENTS

| 5,482,616 | A | 1/1996 | Brahma et al. |
| 2004/0024273 | A1* | 2/2004 | Bottcher ............... C07C 5/10 585/266 |

(Continued)

FOREIGN PATENT DOCUMENTS

| EA | 200702557 A1 | 4/2008 |
| EP | 0002575 | * 6/1979 |

(Continued)

OTHER PUBLICATIONS

EPO Office Action correspondig to application No. 16768791.2-1101; dated May 21, 2019 (Year: 2019).*

(Continued)

*Primary Examiner* — Randy Boyer
*Assistant Examiner* — Juan C Valencia
(74) *Attorney, Agent, or Firm* — Cantor Colburn LLP

(57) ABSTRACT

A hydrogenation catalyst with a small amount of supported metal that is excellent in stability and inhibition of side reactions is provided. The catalyst hydrogenates an aromatic hydrocarbon compound into an alicyclic hydrocarbon compound, and a Group X metal represented by nickel is supported in a composite support including at least alumina and titania. The composite support preferably includes at least an alumina substrate coated with titania. It is also preferable that the Group X metal is prereduced by hydrogen. In the case that the Group X metal is nickel, the nickel content is preferably 5-35 wt % as nickel oxide in the catalyst. The substrate includes, for example, a porous (Continued)

structure formed by a plurality of needle-shaped or column-shaped intertwined three-dimensionally.

4 Claims, 2 Drawing Sheets

(51) Int. Cl.
| | |
|---|---|
| C07C 5/10 | (2006.01) |
| C07C 13/18 | (2006.01) |
| C01G 23/08 | (2006.01) |
| B01J 21/04 | (2006.01) |
| B01J 35/10 | (2006.01) |
| B01J 37/02 | (2006.01) |
| B01J 21/06 | (2006.01) |
| C01G 53/04 | (2006.01) |
| B01J 37/18 | (2006.01) |
| C01F 7/02 | (2006.01) |
| C01F 7/34 | (2006.01) |
| C01G 23/04 | (2006.01) |
| G01N 23/20 | (2018.01) |

(52) U.S. Cl.
CPC ....... B01J 35/1019 (2013.01); B01J 35/1042 (2013.01); B01J 37/0201 (2013.01); B01J 37/0207 (2013.01); C01F 7/34 (2013.01); C01G 23/08 (2013.01); C01G 53/04 (2013.01); C07C 5/10 (2013.01); C07C 13/18 (2013.01); *B01J 37/18* (2013.01); *C01F 7/02* (2013.01); *C01G 23/04* (2013.01); *C01P 2002/30* (2013.01); *C01P 2002/72* (2013.01); *C01P 2004/32* (2013.01); *C01P 2004/54* (2013.01); *C01P 2004/84* (2013.01); *C01P 2006/12* (2013.01); *C01P 2006/14* (2013.01); *C01P 2006/16* (2013.01); *C01P 2006/17* (2013.01); *C07C 2601/14* (2017.05); *G01N 23/20075* (2013.01)

(58) Field of Classification Search
CPC . C07C 13/18; C07C 2601/14; C01P 2004/84; C01P 2002/72; C01P 2006/14; C01P 2006/16; C01P 2006/12; C01P 2004/54; C01P 2004/32; C01P 2002/30; C01P 2006/17; C01G 23/04; C01G 53/04; C01G 23/08; G01N 23/20075
See application file for complete search history.

(56) References Cited

U.S. PATENT DOCUMENTS

| | | | |
|---|---|---|---|
| 2004/0030208 A1 | 2/2004 | Himelfarb et al. | |
| 2006/0009666 A1* | 1/2006 | Ramachandran | C10G 45/36 585/258 |
| 2006/0234861 A1 | 10/2006 | Fukumoto et al. | |
| 2012/0190541 A1* | 7/2012 | Koranne | B01J 21/063 502/439 |
| 2012/0318717 A1* | 12/2012 | Inoue et al. | C10G 45/10 208/216 |
| 2013/0324623 A1 | 12/2013 | Maury et al. | |
| 2014/0031199 A1* | 1/2014 | Chang | B01J 23/005 502/328 |
| 2014/0272642 A1* | 9/2014 | Budge | C01B 3/40 429/423 |

FOREIGN PATENT DOCUMENTS

| | | | |
|---|---|---|---|
| EP | 0002575 B1 | | 6/1979 |
| EP | 0339640 | * | 2/1989 |
| EP | 0339640 A | | 11/1989 |
| EP | 2210664 A1 | | 7/2010 |
| JP | S57-190080 A | | 11/1982 |
| JP | 2001-300328 A | | 10/2001 |
| JP | 2004-524273 A | | 8/2004 |
| JP | 2005-103411 A | | 4/2005 |
| JP | 2010-189332 A | | 9/2010 |
| JP | 2015-188878 A | | 11/2015 |
| RU | 2277079 C2 | | 5/2006 |
| RU | 2391326 C1 | | 6/2010 |
| RU | 2478428 C1 | | 4/2013 |
| WO | 2006111340 A2 | | 10/2006 |
| WO | 2014013784 A1 | | 1/2014 |

OTHER PUBLICATIONS

Extended European Search Report corresponding to Application No. 16768791.2-1101/3275535 PCT/JP2016059106; dated Aug. 14, 2018.
Junko Umezawa, "Characteristics and future potential of hydrogen storage and supply system that utilizes organic hydride as a hydrogen storage material," Petro Tech, 2006, pp. 253-257, vol. 29, No. 4, The Japan Petroleum Institute, Tokyo, Japan.
Yoshimi Okada et al., "Global hydrogen supply chain vision and development of organic chemical hydride hydrogen storage and transportation system," Journal of the Hydrogen Energy Systems Society of Japan, 2008, p. 8, vol. 33, No. 4, Tokyo, Japan.
International Search Report from International Application No. PCT/JP2016/059106, dated Jul. 5, 2016.
International Preliminary Report on Patentability from International Application No. PCT/JP2016/059106, dated Jul. 5, 2016.
JPO Notification of Reasons for Refusal corresponding to JP Application No. 2015-060801; dated Aug. 14, 2018.
FIPS Search Report corresponding to Application No. 2017134680; dated Aug. 22, 2018.
RU Office Action corresponding to Application No. 2017134680; dated Aug. 28, 2018.
EPO Office Action corresponding to Application No. 16768791.2-1101; dated May 21, 2019.
Australian Office Action corresponding to AU Application No. 2016237291; dated Jul. 26, 2019.
Teh C. Ho, et al.,"Ultra-deep hydrodesulfurization on MoS2 and Co0.1MoS2: Intrinsic vs. enironmental factors", Journal of Catalyst 277 (2011) pp. 117-122.
Canadian Office Action for corresponding CA Application No. 2,979,801; dated Apr. 23, 2020.

* cited by examiner

HYDROGENATION CATALYST FOR AROMATIC HYDROCARBON AND HYDROTREATMENT METHOD USING THE CATALYST

BACKGROUND OF THE INVENTION

1. Field of the Invention

The present invention relates to a hydrogenation catalyst for hydrogenating an aromatic hydrocarbon compound into an alicyclic hydrocarbon compound and to a hydrotreatment method using the catalyst.

2. Description of the Related Art

Recently, hydrogen energy is gaining attention as an energy medium. In addition to being clean, hydrogen has an advantage in that it can be produced from any primary energy such as fossil fuel, nuclear power, renewable energy, etc. In order to exploit the energy on a large scale, however, it is necessary to store a large amount of hydrogen or transport hydrogen for a long distance. An organic chemical hydride method is proposed as one technology to address the issue (non-patent documents 1 and 2).

The method converts hydrogen, the lightest gas, into an organic chemical hydride such as liquid methylcyclohexane at normal temperature and normal pressure, by fixing hydrogen to an aromatic hydrocarbon such as toluene through a hydrogenation reaction. The organic chemical hydride is transported to a place of use of hydrogen and stored at the place of use. A dehydrogenation reaction is initiated at the place of use to produce hydrogen as a product and aromatics such as toluene produced in the dehydrogenation reaction are collected and re-used. This method utilizes toluene or methylcyclohexane that are components of gasoline so that hydrogen can be stored and transported in the same manner as gasoline is handled. Thus, the method has an advantage in that existing infrastructure for distribution of gasoline can be used.

Non-patent document 1: "Characteristics and future potential of hydrogen storage and supply system that utilizes organic hydride as a hydrogen storage material," Junko Umezawa, Petro Tech, vol. 29, No. 4, 253-257 (2006)
Non-patent document 2: "Global hydrogen supply chain vision and development of organic chemical hydride hydrogen storage and transportation system," Okada Yoshimi, Masashi Saito, Nobuhiro Onda, Junichi Sakaguchi, Hydrogen Energy System vol. 33, No. 4, p. 8 (2008)

Catalysts in which a Group X metal or a Group VI metal is supported on a support comprised of a porous inorganic oxide such as silica, diatomaceous earth, alumina, etc. has been used in the related art as a hydrogenation catalyst for aromatic hydrocarbon described above. The related-art hydrogenation catalyst allows obtaining catalyst activity and selectivity of a certain degree by supporting the metal in a relatively large amount but is not necessarily satisfactory in respect of inhibition of side reactions and stability.

SUMMARY OF THE INVENTION

The present invention addresses the above issue and a purpose thereof is to provide a hydrogenation catalyst and a hydrotreatment method using the hydrogenation catalyst for hydrogenating an aromatic hydrocarbon compound into an alicyclic hydrocarbon compound that demonstrate excellent stability and inhibition of side reactions with a relatively small amount of metal supported.

The hydrogenation catalyst provided by the present invention to achieve the above purpose is a catalyst that hydrogenates an aromatic hydrocarbon compound into an alicyclic hydrocarbon compound, wherein a Group X metal is supported in a composite support including at least alumina and titania.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1:
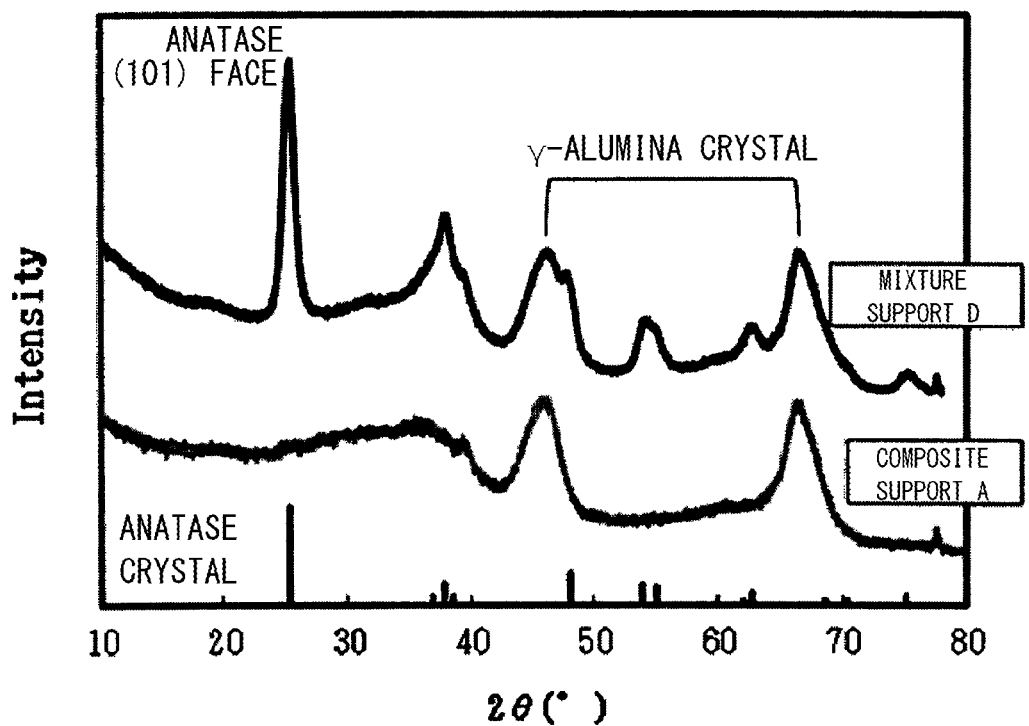
FIG. 1 shows a result of X-ray diffraction analysis of a composite support provided in the hydrogenation catalyst according to an embodiment of the present invention and a comparative mixture support.

The invention will now be described by reference to the preferred embodiments. This does not intend to limit the scope of the present invention, but to exemplify the invention.

1. Hydrogenation Catalyst

A description will be given of a hydrogenation catalyst according to a specific example of the present invention. The hydrogenation catalyst according to the specific example of the present invention is characterized in that a Group X metal is supported on a composite catalyst support comprised of at least alumina and titania. To describe it more specifically, the support for the hydrogenation catalyst according to the specific example of the present invention is comprised of at least two types of metals including alumina (aluminum oxide) and titania (titanium oxide). For example, the surface of an alumina substrate is coated with titania to form the catalyst support. Alumina itself easily forms a porous body having a relatively large specific surface area. Thus, an extremely large specific surface area is secured in a porous composite catalyst support produced by coating the porous body with titanium oxide (hereinafter, simply referred to as composite support).

The alumina substrate need not be of any particular shape, and any of various shapes may be employed. A skeleton structure in which needle-shaped or columnar bodies are intertwined three-dimensionally in a complicated manner to form a porous portion is preferable because a large specific surface area is secured, extensive control of the pore structure is possible, and a mechanical strength is high. As regards a suitable size of needle-shaped or columnar bodies, the aspect ratio (length in the longitudinal direction/equivalent diameter in a cross section perpendicular to the longitudinal direction) is preferably 2.5 or higher, and, more preferably, 5 or higher.

It is desirable that the alumina substrate be synthesized by the pH swing method described later. By forming the substrate using the pH swing method, a substantially homogeneous porous structure, in which a plurality of substantially identically sized needle-shaped bodies mentioned above are intertwined three dimensionally in a complicated manner, can be formed. According to the pH swing method, a substrate formed of an inorganic oxide having a desired porous structure can be obtained by adjusting conditions for synthesis as appropriate.

The pH swing method is a method for synthesis that includes changing the pH of a synthetic solution of inorganic oxide (a source material for alumina) between the acidic side and the alkaline side, thereby swinging the inorganic oxide between the dissolution domain and the precipitation domain and letting particles grow uniformly to a target size. According to the pH swing method, inorganic oxide particles having a desired pore structure (uniform and having desirable pore diameters) are obtained by properly controlling a variety of conditions such as the number of swings, temperature for synthesis, pH and retention time on the acidic and alkaline sides, density of raw materials, and use or non-use of additives such as a particle growth inhibitor. Therefore, conditions for synthesis of inorganic oxide by the pH swing method may be selected as appropriate to serve the purpose of the catalyst.

Synthesis of alumina by the pH swing method is described in details in, for example, JP1-16773, JP2-56283, JP56-120508, JP57-44605, JP Application 2002-97010, JP Application 56-115638, "Ceramics," No. 4, 1998, etc. The disclosures are incorporated herein into the present invention.

The aforementioned titanium oxide for coating the surface of the porous alumina substrate generally has a substantially spherical shape and may be directly attached to the surface of the substrate. It is preferable, however, to ensure that the shape of the titanium oxide cannot be identified by chemically and/or microscopically uniting the alumina substrate with the titanium oxide. We have made a careful study on this issue and found out that by using, as the support for the hydrogenation catalyst adapted to the field of the present invention, a support placed in a condition of not showing a crystalline structure of titanium oxide under X-ray diffraction analysis by coating the surface of an alumina substrate while the titanium oxide is chemically and/or microscopically united with the alumina, high reaction selectivity for a target reaction (e.g., producing methylcyclohexane from toluene) is retrieved and, at the same time, a marked advantage in maintenance of catalyst activity is exhibited.

The term "chemically and/or microscopically united" refers to a condition where the titanium oxide coating the surface of the porous alumina substrate is not merely in physical contact with the substrate surface as in the case of agglomeration or mixing, but forms a strong chemical bond or is bonded to the alumina by covering the substrate surface as extremely minute crystals so that the alumina and the titanium oxide are united. The composite support in the united condition like this shows high catalyst activity inherent in titanium oxide itself without being affected by the chemical properties of the core alumina.

As a result, mere intermediate performance partly originating from alumina and partly from titanium oxide is not hardly exhibited. Side reactions due to alumina composite effect are not promoted, resulting in less disadvantage of lowered reactant selectivity and catalyst degradation. Stated otherwise, the use of a related-art composite of titanium oxide and heterogeneous oxide (a composite where a heterogeneous oxide is used as a binder, a composite produced by coprecipitating a titanium oxide and a heterogeneous oxide) results in the heterogeneous oxide appearing as spots on the surface of the support. Accordingly, catalyst reaction properties originating from both titanium oxide and heterogeneous oxide are exhibited. By way of contrast, in the hydrogenation catalyst according to the specific example of the present invention described above, the primary particle surface of alumina crystal used as a substrate is coated with a thin layer of a hydroxide of titanium, in a hydrogel condition. Therefore, unlike a coating deposited, etc. on a substrate having a pore structure defined by calcination, substantially the entirety of the exposed surface of the support can be populated by titanium oxide regardless of the pore size. Accordingly, only the properties inherent in titanium oxide can be exhibited.

According to the composite support described above, the physical property inherent in the alumina substrate is reflected so that the composite support will possess excellent features inherent in the substrate. In other words, a composite support produced by coating the surface of an alumina substrate with titanium oxide has a large specific surface area and a large pore volume, and has a pore distribution suitable for reactants. Thus, a support provided with both the feature of an alumina substrate with high mechanical strength and the excellent chemical property of titanium oxide having high surface activity can be realized. Titanium, which is expensive and has high density, is used to coat only the surface of the substrate so that the weight is decreased and the cost is significantly reduced as compared to the case of using a high-purity titanium oxide support. It should be noted that the hydrogenation catalyst according to the specific example of the present invention may include, in addition to the composite support, in part a support in which multiple alumina particles and multiple titania particles are united in a mixed condition, instead of being united chemically and/or microscopically.

Titania particles mixed with alumina particles in this case can be considered as titanium oxide particles not chemically and/or microscopically united with the alumina substrate. If titania particles of this type are found in the support used in the hydrogenation catalyst according to the specific example of the present invention, a main peak (appearing at a diffraction angle $2\theta=25.3\pm0.2°$ in an ordinary device using a CuK$\alpha$ ray as an X ray source) corresponding to the (101) plane of anatase structure indicating the presence of titania may be detected under X-ray diffraction analysis, depending on the proportion of titania particles included.

In the support used in the hydrogenation catalyst according to the specific example of the present invention, however, the peak intensity of a peak corresponding to the (101) plane of anatase structure is, even if it is detected under X-ray diffraction analysis, extremely small as compared to the case of a support in which titania, having anatase structure, is merely physically mixed with alumina. This is because titania particles of this type are, even if they are found in the support used in the hydrogenation catalyst according to the specific example of the present invention, merely in a minor amount in relation to the entire titanium oxide contained in the support. The titania particles assumed here are considered to be synthesized from the same titanium material as used in the support for the hydrogenation catalyst according to the specific example of the present invention and to be cleaned. The particles are considered to have anatase structure calcinated at the same temperature as the support used in the hydrogenation catalyst according to the specific example of the present invention, ultimately.

An example of the "chemically and/or microscopically united" condition is a repeat distance in the crystal lattice plane of titanium oxide on the surface of alumina substrate that is preferably 50 Å or less, and, preferably, 40 Å or less, and, most preferably, 20 Å or less. Generally, when a substance with a small repeat distance in a crystal lattice plane such as this is measured by an X-ray diffracting device, diffraction lines of the substance overlap other diffraction lines and the limit of measurement is exceeded. As a result, even if an attempt is made to measure the surface of the composite support by a commonly used X-ray diffraction device, the neighborhood of the main peak $2\theta=25.3°$ of anatase structure of titanium oxide may not be detected. Conversely, if the neighborhood of the main peak $2\theta=25.3°$ of titanium oxide is not detected by a commonly used X-ray diffraction device in spite of the existence of titanium oxide on the surface of alumina, it is concluded that the specimen in question is a composite support. Of course, not all supports used in the hydrogenation catalyst according to the specific example of the present invention demonstrate absence of detection of the neighborhood of the main peak $2\theta=25.3°$ of titanium oxide in a measurement made by an X-ray diffraction device.

Another example of the "chemically and/or microscopically united" condition is inability to clearly distinguish particles of alumina from those of titanium oxide in a high-magnification image (for example, 2,000,000-fold magnification) of a transmission electron microscope (TEM) (hereinafter referred to simply as "TEM image"). If the alumina and the titanium oxide are chemically and microscopically separate, the substances will respectively form primary particles with different crystalline systems, which will be separately recognizable on basis of the crystal lattice plane spacing in TEM images. If the alumina and the titanium oxide are chemically united or the titanium oxide covers the surface of the alumina substrate as extremely fine crystals, the substances cannot be identified as being separate.

Therefore, in the case where the particles of alumina cannot be distinguished clearly from those of titanium oxide on the basis of the crystal lattice plane spacing in TEM images from an ordinary TEM device in spite of the existence of titanium oxide on the surface of the alumina substrate, it is concluded that the specimen in question the composite support described above. Of course, this does not necessarily mean that particles of alumina cannot be distinguished clearly from those of titanium oxide in TEM images of all specimens of the composite support described above.

The porosity of the above-described composite support originates from the pore structure inherent in the alumina itself. In addition, the surface of the alumina is coated with a thin layer of titanium oxide so that the porosity originates in part from the outer surface condition of the titanium oxide. The porous structure of the above-described composite support is determined by both. In the case of a support comprised only of substantially homogeneous spherical titanium oxide particles, the specific surface area is substantially determined by the particle size. Due to poor thermal stability of titanium oxide itself, titanium oxide particles aggregate in association with heating, resulting in large particles and a decrease in the specific surface area. In the composite support described above, the surface condition of alumina, which is excellent in thermal stability, is substantially directly reflected. Therefore, the specific surface area is almost completely determined at the stage of porous alumina substrate and a composite support in which the specific surface area is substantially maintained even when heated is available.

As described above, an extremely large specific surface area is obtained by exercising appropriate control in the composite support used as a support for the hydrogenation catalyst according to the specific example of the present invention. In order for the catalyst support to have an excellent property, the specific surface area is preferably 100 $m^2/g$ or larger, and, more preferably, 130 $m^2/g$ or larger, and, still more preferably, 150 $m^2/g$ or larger. The specific surface area in this case can be measured by, for example, the mercury intrusion porosimetry, nitrogen adsorption porosimetry, etc.

The hydrogenation catalyst according to the specific example of the present invention is configured such that a Group X metal compound as a catalytic metal compound is supported on the composite support described above. The Group X metal is exemplified by nickel compounds. Nickel nitrate, basic nickel carbonate, etc. are particularly preferable. The amount supported (content) of the Group X metal compound is preferably in the range of 3-35 mass %, and, more preferably, in the range of 6-20 mass % in relation to the entire catalyst (i.e., a total of the composite support described above and the Group X metal compound in terms of oxides; hereinafter, the same definition is used). If the amount of metal compound supported is less than 5 mass %, sufficient catalytic activity may not be obtained. Meanwhile, the metal compound may be supported in an amount of 35 mass % or larger. Since a hydrogenation reaction is an exoergic reaction, however, an excessive increase in the amount of metal supported results in a high temperature in the catalyst layer and, consequently, acceleration of production of impurities.

2. Method of Manufacturing Hydrogenation Catalyst

A description will now be given of a method of manufacturing a hydrogenation catalyst according to a specific example of the present invention described above. The method of manufacturing the hydrogenation catalyst according to the specific example of the present invention includes a substrate preparation step, a coating step, a cleaning step, a molding step, a calcination step, an impregnation step, and a drying step. The steps will be described in the order of execution.

Substrate Preparation Step

A hydrosol, a hydrogel, a xerogel, etc. containing hydrated alumina particles can be used as a source of alumina in the substrate of the support for the hydrogenation catalyst according to the specific example of the present invention. Boehmite, quasi-boehmite, alumina gel, etc. or a mixture thereof can be used as a crystalline system for the hydrated alumina particles. The method of preparing hydrated alumina particles is not limited to any particular method but it is preferable to synthesize the hydrated alumina particles by the pH swing method described above. By synthesizing the hydrated alumina particles, alumina having a homogeneous shape and a pore sharpness of 60% or higher can be obtained. The hydrosol of the hydrated alumina particles manufactured by the pH swing method contains contaminant ions originating from the source alumina compound. Therefore, contaminant ions may be removed by cleaning as necessary, prior to the step of titanium hydroxide coating described later.

It is preferable that the pore volume of the hydrated alumina particles manufactured in this way be within the range of 0.36-1.10 mL/g after the particles are calculated at 500° C. for 3 hours as described later. If the pore volume is less than 0.36 mL/g, the packing density demonstrated when the catalytic metal is supported will be high (e.g., in excess of 1.1 g/mL) so that the withstand load of existing hydrogenation reaction devices may be exceeded. Meanwhile, if the pore volume exceeds 1.10 mL/g, the catalytic particle side crushing strength (SCS) demonstrated when the catalytic metal is supported will be low (e.g., less than 0.6 kg/mm in terms of the diameter of 1 mm), falling short of a practical strength.

The pore sharpness demonstrated after 3 hours of calcinating the hydrated alumina particles is preferably 60% or higher and, more preferably, 70% or higher. "Pore sharpness" is a numerical value that serves as a measure of uniformness of pore diameters. The closer the pore sharpness to 100%, the more uniform the pore diameters of the catalyst and the support. The pore sharpness can be calculated from an accumulated pore distribution curve determined by mercury intrusion porosimetry. More specifically, the pore diameter at 50% of the pore volume (median diameter) is determined. The partial pore volume (PVM) located in the ±5% pore diameter range of the logarithmic value of the median diameter is then determined. The pore sharpness is determined according to expression 1 below, using the partial pore volume (PVM) and the pore volume (PVT).

$$\text{Pore sharpness (\%)} = (PVM/PVT) \times 100 \qquad \text{Expression 1}$$

Coating Step

Coating is a process of obtaining hydrated alumina particles coated with the titanium hydroxide by adding, in predetermined temperature and pH ranges, an aqueous solution of acid compound containing titanium and an aqueous solution containing an alkali compound to a hydrosol containing hydrated alumina particles formed by the aforementioned pH swing method, and by coating the surface of the hydrated alumina particles with particles of the hydroxide of titanium, maintaining a constant pH. The term "acid compound containing titanium" (hereinafter, also referred to as "titanium compound" simply) is preferably titanium sulfate, titanyl sulfate, titanium chloride, titanium peroxide, titanium oxalate, titanium acetate, etc.

To describe the method of adding an aqueous solution of titanium compound to the hydrated alumina particles in details, an aqueous solution of titanium compound and an aqueous solution containing an alkali compound are added, suitably simultaneously and continuously, to a hydrosol in which the hydrated alumina particles are dispersed, under the temperature and the pH condition described later. The temperature in this process is preferably in the range of 10-100° C., and, more preferably, in the range of 15-80° C. If the hydrated alumina particles are manufactured by the pH swing method described above and the aqueous titanium compound solution is added immediately subsequently, for example, the temperature will be approximately within the range of 50-100° C. If the hydrated alumina particles are manufactured and then stored so that the temperature drops, the temperature will be approximately within the range of up to 50° C. The temperature during addition is determined by the temperature at which the hydrated alumina particles are manufactured.

The pH in this process is preferably in the range of pH 4.5-6.5. The aqueous solution of titanium compound and the aqueous solution containing an alkali compound are added, suitably simultaneously and continuously, maintaining the pH at constant level as much as possible. In case a coating reactor vessel of a large capacity is used, it is difficult to maintain the pH completely at a constant level. The term "maintained at a constant level" shall encompass cases of controlling the pH to approximate a target pH value as much as possible. For example, it is preferable to control the pH to be accommodated within the range of ±0.5 in relation to the target pH value. By controlling the pH condition in this way, the surface of the hydrated alumina particles is suitably coated with the titanium hydroxide particles. In this process, the isoelectric point of the hydrated alumina particles coated with the titanium hydroxide changes depending on the amount of coating. Table 1 below shows results of measuring isoelectric points at different amounts of titanium hydroxide coating.

TABLE 1

| Amount of titanium hydroxide particle coating [mass %] | Results of isoelectric point (pH) measurement |
| --- | --- |
| 0 | 10.0 |
| 10 | 9.2 |
| 20 | 8.5 |
| 30 | 7.8 |
| 40 | 7.2 |
| 50 | 6.6 |
| 100 | 4.2 |

Referring to Table 1, the amount of titanium hydroxide particle coating is given by a mass proportion (mass %) of the titanium hydroxide particles in relation to a total of the hydrated alumina particles and the titanium hydroxide particles in terms of oxides. 0 mass % and 100 mass % of the titanium hydroxide particle coating represent a case comprising only of hydrated alumina particles and a case comprising only of titanium hydroxide particles, respectively. In the following description, the term "amount of titanium hydroxide particle coating" means a mass proportion (mass %) of the titanium hydroxide particles in relation to a total of the titanium hydroxide particles and the hydrated alumina particles in terms of oxides. Isoelectric points were measured by the electrophoretic light scattering method using HLS-8000 from Otsuka Electronics. Based on the relationship between the pH and the zeta potential thus measured, the pH that gives 0 zeta potential is identified and defined as the isoelectric point.

Principally, the range of pH in which the surface of the hydrated alumina particles with particles of the hydroxide of titanium may exceed pH 4.2, which is the isoelectric point of 100% titanium hydroxide particles and may be below the isoelectric point corresponding to the associated density of titanium hydroxide particles (the amount of titanium hydroxide coating), as indicated in Table 1. In the case that the density of the titanium hydroxide particles is 10 weight %, pH will be less 9.2.

To coat the surface of the hydrated alumina particles with the hydroxide of titanium uniformly and firmly, however, the range of pH 4.5-6.5 is preferable, as mentioned above. This is because, by ensuring that the pH is 4.5 or higher, the zeta potential of the titanium hydroxide particles will be −5.0 mV or below (absolute value of 5.0 mV or higher), and, by ensuring that the pH is 6.5 or lower, the zeta potential of the hydrated alumina particles will be 20 mV or higher (absolute value of 20 mV or higher), so that the titanium hydroxide maintained at a negatively charged condition and the hydrated alumina particles maintained at a positively charged condition are bonded to each other firmly. By using the pH range described above, the titanium hydroxide is strongly attracted by the surface of the hydrated alumina particles by the attraction between positive and negative charges so that the surface is coated efficiently and firmly.

The coating operation is preferably performed within the margin of pH variation of ±0.5 around the pH indicated by expression 2 below and within the range of 5 minutes to 5 hours of duration of coating. T denotes the amount of coating (mass %) of the titanium hydroxide in the composite support.

$$pH=6.0-0.03 \times T \qquad \text{Expression 2}$$

By performing the coating operation under the above pH condition, the total of the absolute values of zeta potential of the titanium hydroxide particles and hydrated alumina particles is effectively maintained substantially at the maximum value so that the surface of the hydrated alumina particles is coated more firmly by the titanium hydroxide. Expression 2 is derived by measuring the relationship between the zeta potentials of the titanium hydroxide particles and the hydrated alumina particles, respectively, and the pH, and by deriving the condition that distances the positive and negative zeta potentials effectively, using the amount of coating of the titanium hydroxide as a variable.

If the duration of coating of the titanium hydroxide is less than 5 minutes, it is difficult to maintain the pH value at a desired pH value completely constantly in a coating reactor vessel of a large capacity. As a result, it is difficult to coat the hydrated alumina particles with the titanium hydroxide uniformly and firmly. Meanwhile, the duration in excess of 5 hours results in a significant decrease in the efficiency of coating of the hydrated alumina particles. Characteristically, the titanium hydroxide coating the surface of the hydrated alumina particles does not exhibit an anatase crystal structure, which is a titanium hydrate, under X-ray diffraction analysis. This will be explained in details in connection with the calcination step described later.

The amount of particles of the hydroxide of titanium coating the surface of the hydrated alumina particles is preferably within the range of 5-40 mass % in relation to the entire composite support, and, more preferably, within the range of 10-35 mass %. If the amount of coating is less than 5 mass %, the advantage of adding the titanium hydroxide may not be fully exhibited. The amount of coating in excess of 40 mass %, produces aggregation of the titanium hydroxide, preventing the surface of the hydrated alumina particles from being coated uniformly.

Cleaning Step

The reaction solution that remains after the surface of the hydrated alumina particles is coated with the particles of the hydroxide of titanium generally contains contaminant ions including positive ions like sodium and ammonia ions and negative ions like sulfate and chlorine ions. Therefore, the hydrated alumina particles coated with the titanium hydroxide obtained in the coating step is cleaned in the cleaning step. It is possible to remove or reduce these contaminant ions in the cleaning process. Preferably, the particles are cleaned by water and filtered, using a suction filter, an Oliver filter, a pressure filter, etc.

Molding Step

The hydrate alumina particles coated with the titanium hydroxide obtained in the cleaning step are dehydrated until the moisture is in an amount that allows the particles to be molded. Dehydration is generally performed by mechanical solid-liquid separation using pressure filtration, suction filtration, centrifugal filtration, etc. For example, the particles may be dried by using surplus heat, or dehydration and drying may be combined. After the dehydration process, the particles are molded by a molding machine to a shape suitable for the purpose of use, such as the shapes of columns, clovers, cylinders, and spheres so as to obtain a molded hydrated alumina particle product coated with titanium hydroxide.

Calcination Step

Calcination is a step of preparing a support coated with titania by calcinating the molded hydrated alumina particle product coated with titanium hydroxide obtained in the molding step described above to change titanium hydroxide into titanium oxide. The ambient temperature during calculation may be preferably within the range of 100-600° C., and, more preferably, within the range of 120-500° C. An ambient temperature of below 100° C. requires too much time for calcination and so is not practical. If the temperature exceeds 600° C., a crystal form of anatase begins to be observed so that the titania coating will not be uniform. A characteristic of the support obtained by coating alumina with titania by the above method is that the specific surface area of the support coated with titania tends to be larger than the specific surface area of the hydrated alumina particles of the substrate.

As mentioned above, the titanium hydroxide coating the surface of the hydrated alumina by the above method does not characteristically exhibit an anatase crystal structure under X-ray diffraction analysis. If the neighborhood of the main peak $2\theta=25.3°$ C. of anatase is detected under a commonly used X-ray diffracting device, it means that an aggregate of titania is present. In this case, it cannot be said that coating is optimally performed. If the peak is not detected, however, it is considered that the surface of the hydrated alumina particles is firmly and uniformly coated with the titanium hydroxide. It is further suggested that the repeat distance in the crystal lattice plane of the titanium hydroxide is 50 Å or less.

Meanwhile, the titanium hydroxide coating deviating from the above condition is likely to exhibit a crystal structure of anatase, which is a titanium hydrate, under X-ray diffraction analysis. The likelihood is also high that the coating is not firm. If the hydrated alumina particles are coated with the titanium hydroxide in an amount of 30 mass % in terms of oxides by maintaining the pH at 8.0, the titanium hydroxide and the titania coated hydrated alumina particles are both negatively charged and repulse each other, resulting in less firm coating.

Impregnation Step

An impregnation step is a step of impregnating the alumina support with the titania coating obtained in the calcination step described above (hereinafter, also referred to as titania coated alumina support) with an aqueous solution containing a Group X metal compound as a catalytic metal compound. The Group X metal compound supported by impregnation with the aqueous solution containing the catalytic component is preferably aged so that the active metal is uniformly and stably supported in the titania coated alumina support. The term "aging" means impregnating the support with the aqueous solution containing the catalytic component and allowing the support to keep still in that condition. The duration of aging is preferably within the range of 10 minutes to 24 hours.

Drying Step

The titania-coated alumina support impregnated with the aqueous solution containing the catalytic component in the impregnation step described above is dried in order to cause the catalyst component and the sugar group to become stabilized in the titania coated alumina support. The drying temperature is preferably within the range of 100-500° C. After drying, the support may continue to be heated for calcination. The duration of drying is preferably within the range of 0.5-24 hours. By performing the series of steps described above, a hydrogenation catalyst exhibiting a high catalytic activity is obtained.

3. Hydrotreatment Method

A description will be given of a method of performing a hydrotreatment using the hydrogenation catalyst described above. A hydrotreatment device of a fixed bed system is preferable. The device may be configured for any of various conditions under the constraints of the structure of the reactor vessel etc. Generally, it is preferable to configure the liquid hourly space velocity (LHSV) to be within the range of 1-10 hr-1, the pressure to be within the range of 0.3-15 MPaG, and the temperature to be within the range of 100-350° C.

The compact bulk density (CBD) of the catalyst is preferably within the range of 0.5-1.1 g/mL, and, more preferably, within the range of 0.5-1.0 g/mL. The compact bulk density (CBD) of less than 0.5 g/mL results in low catalyst side crushing strength (SCS) of the catalyst (e.g., 0.6 kg/mm or less), which may fall short of the practical strength for the catalyst. Meanwhile, the CBD in excess of 1.1 g/mL makes it difficult to fill existing hydrogenation facilities and is not favorable, too.

In the present invention, the compact bulk density (CBD) was measured as described below. First, a catalyst fractionated between 30 to 80 (mesh) through the use of a sieve is dried at 120° C. for 3 hours, then collected in an amount of about 30 g and weighed precisely with an analytical balance. A measuring cylinder made of glass and having an inner diameter of 21 mm and a volume of 50 ml is filled with the fractions. Then, the measuring cylinder is tapped through the use of a vibrator to measure a volume at the minimum bulk. The compact bulk density (CBD) is determined by dividing a mass determined by precisely weighing the catalyst by the volume value at the minimum bulk.

To perform a hydrotreatment process using the hydrogenation catalyst of the present invention described above, it is preferable to perform a preprocess of hydrogen reduction for activation of the catalytic metal. More specifically, a nitrogen gas is introduced into the hydrogenation reaction device filled with the hydrogenation catalyst so as to purge the oxygen in the system. The nitrogen gas is switched to a hydrogen gas for hydrogen reduction. This allows the hydrogenation catalyst to exhibit its activity effectively at a relatively early stage.

The catalyst subjected to the preprocess in this way functions as a hydrogenation catalyst in the hydrogenation step for aromatic compound in the organic chemical hydride method. By introducing a synthesized gas of a hydrogen density of about 30-70 vol % produced in a shift reaction device for a coal gasification process along with an aromatic hydrocarbon, for example, the aromatic hydrocarbon can be converted into an alicyclic hydrocarbon.

Examples of aromatic compounds used in the hydrogenation step include benzene, toluene, xylene, naphthalene, methylnaphthalene, anthracene, etc. Toluene is preferable because it has a boiling point and a melting point that make it possible to maintain a liquid phase without using a solvent. The reaction product obtained in the hydrogenation step for aromatic compound is subjected to vapor-liquid separation after being cooled so that the unreacted hydrogen and the subgenerated light gas are separated and removed, resulting in a hydrogenated aromatic compound as a means of storing and transporting hydrogen.

Embodiment

We experimented hydrogenating toluene into methylcyclohexane by using the hydrogenation catalyst in which nickel is supported on the composite support produced by coating the surface of alumina substrate with titanium oxide. More specifically, an aqueous aluminum sulfate solution of 8 mass % in terms of $Al_2O_3$ was added to a vessel containing hot water heated to 80° C. so that the pH of the solution is 2.5. After 5 minutes, an aqueous sodium aluminate solution of 19 mass % in terms of $Al_2O_3$ was added so that the pH of the synthetic solution is 9. Subsequently, by repeating twice an operation of adding the same aqueous aluminum sulfate solution so that the pH of the synthetic solution is 3 and then adding the same aqueous sodium aluminate solution so that the pH of the synthetic solution is 9, a hydrosol of hydrate alumina particles of 1.8 mass % in terms of $Al_2O_3$ was obtained.

Contaminant ions contained in the hydrosol were removed through a cleaning operation of subjecting the hydrosol obtained above to suction filtration, adding water again to the collected gel, and repeating suction filtration. The hydrosol H of the cleaned hydrated alumina particles obtained was adjusted to 1.8 mass % in terms of $Al_2O_3$ and was maintained at 60° C. An aqueous titanium sulfate solution of a density in terms of Ti of 1.7 mass % was first continuously added to lower the pH of the solution to 5.6. Starting at that point of time, the aqueous titanium sulfate solution was continuously added, and, at the same time, the aqueous sodium hydroxide solution of 8 mass % was also continuously added so that the pH of the hydrosol is maintained at 5.6±0.1. In this way, the source materials were added to the hydrosol continuously over a period of 1 hour. A composite hydrosol in which the surface of hydrated alumina particles is coated with particles of titanium hydroxide was ultimately obtained.

The composite hydrosol coated with the titanium hydroxide obtained above was cleaned by the same method as used to obtain the hydrosol H of hydrate alumina particles described above and contaminant ions were removed. The hydrosol was then dehydrated and subjected to humidity conditioning through suction filtration until the hydrosol is capable of being extrusion molded. The hydrogel was molded to a columnar shape by using an extrusion molding machine. The molded product was dried for 3 hours in an air atmosphere of 120° C. and, further, calcinated for 3 hours in an air atmosphere of 500° C. A columnar composite support A having a diameter of 1.3 mm was obtained through the above operation. The amount of titania contained in the composite support A was measured by ICP emission spectrometric analysis and it was found that the proportion of titania content in terms of oxides was 15 mass %.

For the purpose of comparison, an alumina support B was obtained by subjecting the cleaned hydrosol H of hydrated alumina particles to dehydration, humidity conditioning, molding, drying, and calcination in the same manner as described above except that the titanium hydroxide coating is not provided. Further, for the purpose of comparison, the aqueous titanium sulfate solution and the aqueous sodium hydroxide solution used for titanium hydroxide coating were continuously added to a vessel containing hot water heated to 60° C. so that the pH of the solution is maintained at 5.6±0.1, in the same manner as when preparing the composite support A described above and a hydrosol of titanium hydroxide was obtained. This is followed by the steps of cleaning through calcination, similar to the case of processing the composite hydrosol as described above, to obtain a titania support C. The alumina support B and the titania support C obtained above were pulverized. The titania support C was uniformly mixed in the alumina support B such that the content of titania is 15 mass %, and a mixture composite D was obtained.

Aspect Ratio

The alumina support B corresponding to the substrate of the composite support A was subjected to TEM analysis using H-9000NAR from Hitachi High Technologies. It was confirmed in a 1,000,000-fold magnification image of TEM analysis that the alumina support B is comprised of needle-shaped primary particles. The length of the longer sides and the shorter sides of a total of 50 such needle-shaped bodies with identifiable shapes were measured. It was found that the aspect ratio of the needle-shaped bodies was about 5.

X-Ray Diffraction

The composite support A and the mixture support D were subjected to X-ray diffraction analysis using SmartLab (an X-ray diffraction analysis device from Rigaku Corporation) with an X-ray output of 40 kV and 40 mA, and using CuKα as an X-ray source. FIG. 1 shows an X-ray diffraction analysis chart of the composite support A and the mixture support D. In the mixture support D, a peak of particularly high intensity corresponding to the (101) plane of the anatase structure of titania is observed at 2θ=25.3°. In the composite support A, no peaks corresponding to titania were observed despite the fact that the titania content is the same as that of the mixture support D.

Pore Volume and Sharpness

Figure 2:
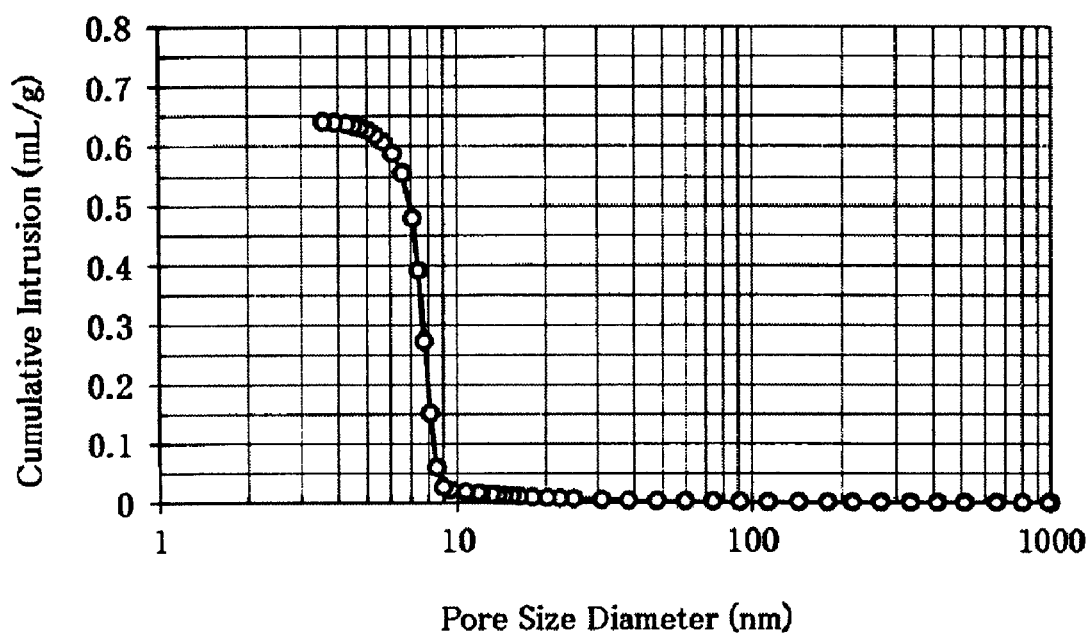
FIG. 2 is a graph showing pore distribution of an alumina support corresponding to a skeleton of a composite support used in the hydrogenation catalyst according to the embodiment of the present invention.

The pore volume and pore distribution of the alumina support B corresponding to the substrate of the composite support A were measured by mercury intrusion porosimetry that pressurizes the support to a measurement pressure of 414 MPa, using AutoPore IV9520 from Shimazu Corporation. FIG. 2 shows a chart of pore distribution. The pore volume of the alumina support B was 0.64 mL/g. The pore diameter sharpness of the alumina support B calculated from the data in accordance with [expression 1] was 70%.

Specific Surface Area

The specific surface area of the composite support A analyzed by the BET method was 408 m2/g.

Subsequently, the composite support A obtained by the above method was fractionated. One of the fractions was immersed in and impregnated with an aqueous nickel nitrate solution of 53.5 mass % and aged by being kept still for 3 hours in that condition. Subsequently, the support was dried for 3 hours in an air atmosphere of 120° C. and was further calcinated for 3 hours in an air atmosphere of 450° C. In this way, the hydrogenation catalyst of sample 1 in which nickel is supported on the composite support A was prepared. The amount of nickel supported in the catalyst of sample 1 was determined to be 22 mass % in terms of NiO by ICP emission spectrometric analysis.

Hydrogenation catalysts of samples 2-4 with different amounts of nickel supported (the amounts of Ni supported in terms of NiO of 10.0 mass % (sample 2), 7.5 mass % (sample 3), 5.0 mass % (sample 4)) were prepared from the rest of fractionated composite support A in the same manner as sample 1 above except that the density of the aqueous nickel nitrate solution is varied. Further, for the purpose of comparison, a commercially available hydrogenation catalyst, in which nickel in an amount of 22 mass % in terms of NiO is supported in diatomaceous earth as a support, was prepared as sample 5.

The hydrogenation catalysts of samples 1-4 were subjected to a preprocess of hydrogen reduction by maintaining them in a condition of normal pressure and 450° C. for 15 hours in a hydrogen atmosphere. The hydrogenation catalyst of sample 5 was already subjected to preparatory reduction and so was not subjected to hydrogen reduction as described above. Subsequently, 21.3 mL of α-alumina (from Tipton Corp, product number 1 mmφ) was mixed with 7.5 g (10.7 mL) each of the hydrogenation catalysts of samples 1-5. Cylindrical reaction tubes each having an inner diameter of 21.2 mm and a height of 880 nm were filled with the mixtures.

Figure 3:
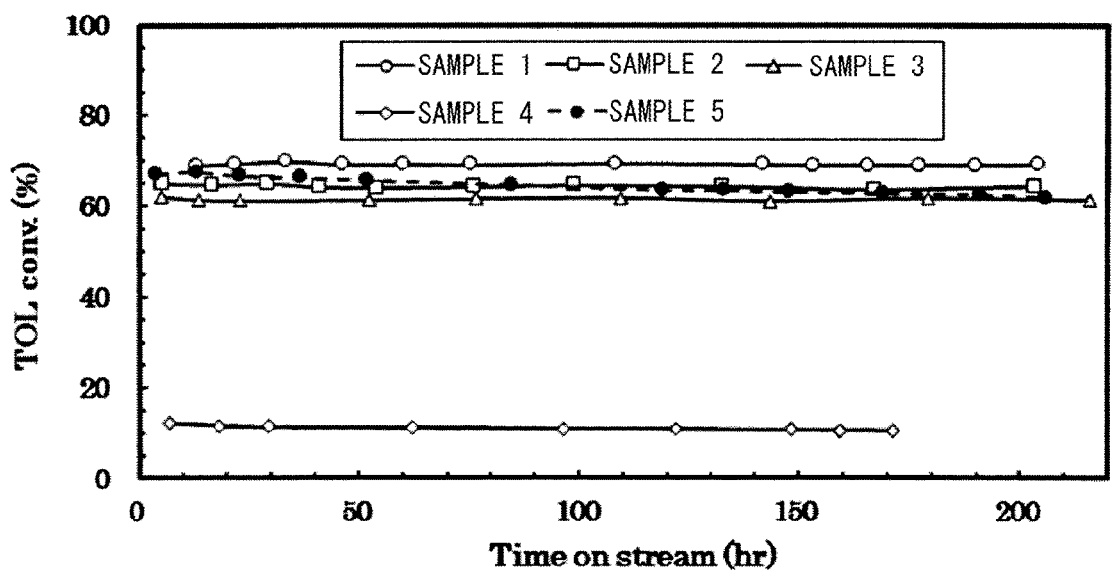
FIG. 3 shows a time-dependent change in toluene conversion of hydrogenation catalysts of samples prepared in the embodiment.
Figure 4:
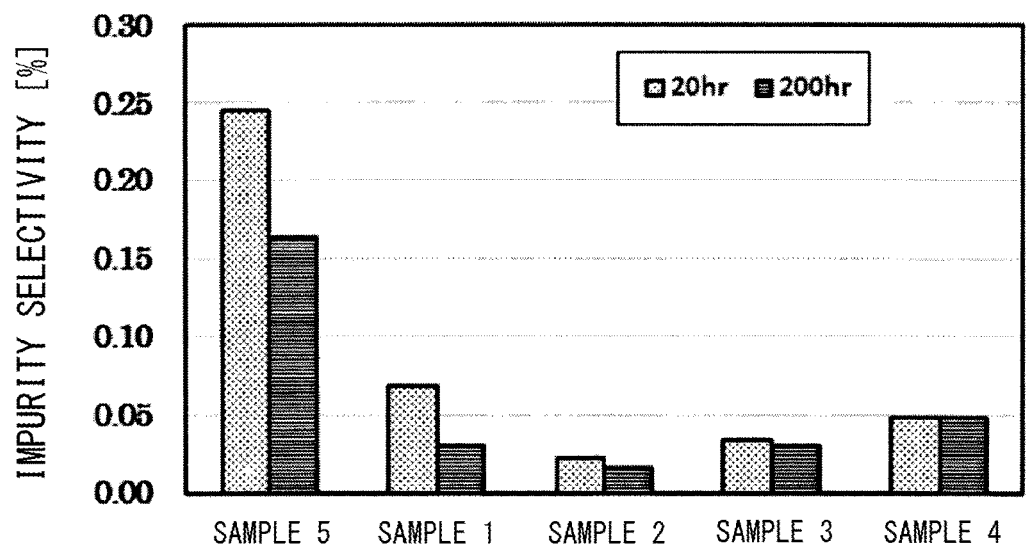
FIG. 4 shows impurity selectivity of the hydrogenation catalysts of the samples prepared in the embodiment.

The hydrogenation catalysts of the samples were subjected to hydrogen reduction for 15 hours in a hydrogen atmosphere of 100 vol % H2 under a pressured condition at a preset temperature of 180° C. Subsequently, toluene was hydrogenated by being supplied in a gas flow rate of toluene/H2/N2=7.1/14.0/9.0 [NL/hr] (at LHSV (toluene) of 3.2) to the hydrogenation catalysts under a pressured condition at a preset temperature of 140° C. The result is shown in Table 2. FIG. 3 shows a time-dependent change in toluene conversion and FIG. 4 shows a comparison of impurity selectivity. The data indicated as being obtained for sample 4 after 200 hr is data obtained after 170 hr.

TABLE 2

| Sample | Amount of Ni supported (in terms of NiO) [mass %] | After 20 hr | | | After 200 hr | | |
| --- | --- | --- | --- | --- | --- | --- | --- |
| | | Toluene conversion [%] | MCH selectivity [%] | Impurity selectivity [%] | Toluene selectivity [%] | MCH selectivity [%] | Impurity selectivity [%] |
| 1 | 22.0 | 69.3 | 99.81 | 0.07 | 69.1 | 99.91 | 0.03 |
| 2 | 10.0 | 64.9 | 99.80 | 0.02 | 64.4 | 99.81 | 0.02 |
| 3 | 7.5 | 61.2 | 99.80 | 0.03 | 61.4 | 99.80 | 0.03 |
| 4 | 5.0 | 11.5 | 99.62 | 0.05 | 10.6 | 99.58 | 0.05 |
| *5 | 22.0 | 66.6 | 99.59 | 0.25 | 61.9 | 99.59 | 0.16 |

*Sample labeled with * is a that of comparative example.

Toluene conversion is calculated from toluene density [mass %] in the solution before and after the reaction. The MCH selectivity is defined as the amount of MCH generated [mass %]/the amount of toluene reacted [mass %], and the impurity selectivity is defined as the amount of impurities generated (entirety) [mass %]/the amount of toluene reacted [mass %]. The sum of the MCH selectivity and the impurity selectivity does not amount to 100% because of the presence of methylcyclohexene (which results from a double bond at one side of cyclo ring of MCH), which is a reaction intermediate.

Table 2 and FIG. 4 show that the impurity selectivity is controlled to be about ⅓ or less, as compared to the hydrogenation catalyst of sample 5 (comparative example), in the hydrogenation catalysts of samples 1-4 in which nickel is supported in an amount of 5.0 mass % or more in terms of NiO in the composite support A, which is produced by coating the alumina substrate with titania, demonstrating that the hydrogenation catalysts of samples 1-4 are excellent in inhibiting side reactions.

Table 2 and FIG. 3 further show that the hydrogenation catalysts of samples 1-3, in which nickel is supported in an amount of 7.5 mass % or more in terms of NiO in the composite support A, which is produced by coating the alumina substrate with titania, are characterized by high toluene conversion and substantially zero changes in toluene conversion, demonstrating that the activity and stability of the hydrogenation catalysts of samples 1-3 are extremely high. The toluene conversion after 20 hr of the hydrogenation catalyst of sample 5 (comparative example) in which nickel is supported in diatomaceous earth is 66.6%, which is certainly favorable. However, the conversion drops to 61.9% after 200 hr, meaning that the catalytic activity drops.

What is claimed is:

1. A hydrogenation catalyst that hydrogenates an aromatic hydrocarbon compound into an alicyclic hydrocarbon compound, wherein a Group X metal is supported in a composite support including at least alumina and titania, wherein the composite support comprises a substrate comprising primary particles of alumina crystal, an entirety of a surface of the primary particles being coated with titania, and wherein a repeat distance in a crystal lattice plane of the titania on the surface of the primary particles is 50 Å or less, and wherein the hydrogenation catalyst is a reduced hydrogenation catalyst, which is a reaction product of the hydrogenation catalyst and hydrogen, and the reduced hydrogenation catalyst is activated by the hydrogen.

2. The hydrogenation catalyst according to claim 1, wherein the Group X metal is nickel, and the nickel content in the hydrogenation catalyst before reduction of the hydrogenation catalyst 5-35 wt % as nickel oxide.

3. The hydrogenation catalyst according to claim 1, wherein the substrate includes a porous structure formed by a plurality of needle-shaped or column-shaped primary particles of alumina crystal coated with titania, the needle-shaped or column-shaped primary particles being intertwined three-dimensionally.

4. A hydrotreatment method for an aromatic hydrocarbon, comprising:

contacting an activated hydrogenation catalyst with a source gas containing an aromatic hydrocarbon and hydrogen under reaction conditions in which a temperature is within the range of 100-350° C., a pressure is adjusted to 0.3-15 MPa by using a source gas containing hydrogen, and the aromatic hydrocarbon is supplied at a liquid hourly space velocity (LHSV) of 1-10 $hr^{-1}$, thereby producing an alicylic hydrocarbon compound, wherein the activated hydrogenation catalyst is activated by reducing a hydrogenation catalyst, in which a Group X metal is supported in a composite support including at least alumina and titania, by hydrogen, wherein the composite support comprises a substrate comprising primary particles of alumina crystal, an entirety of a surface of the primary particles being coated with titania, and wherein a repeat distance in a crystal lattice plane of the titania on the surface of the primary particles is 50 Å or less.

* * * * *